US012788522B2

(12) United States Patent
Khorasani et al.

(10) Patent No.: US 12,788,522 B2
(45) Date of Patent: Nov. 10, 2026

(54) STERILE DRAPE

(71) Applicant: Auris Health, Inc., Santa Clara, CA (US)

(72) Inventors: Omid Khorasani, Los Altos, CA (US); Santiago Binuya Beltran, Murrieta, CA (US); Stephen Christopher Kreck, II, Pottstown, PA (US); Amanda Lee Richards, Newburyport, MA (US)

(73) Assignee: Auris Health, Inc., Santa Clara, CA (US)

( * ) Notice: Subject to any disclaimer, the term of this patent is extended or adjusted under 35 U.S.C. 154(b) by 230 days.

(21) Appl. No.: 18/737,682

(22) Filed: Jun. 7, 2024

(65) Prior Publication Data

US 2025/0375257 A1 Dec. 11, 2025

(51) Int. Cl.
*A61B 46/10* (2016.01)
*A61B 34/00* (2016.01)
*A61B 46/00* (2016.01)

(52) U.S. Cl.
CPC .............. *A61B 46/10* (2016.02); *A61B 34/74* (2016.02); *A61B 46/40* (2016.02); *A61B 2034/742* (2016.02)

(58) Field of Classification Search
CPC ... A61B 2034/742; A61B 34/74; A61B 46/10; A61B 46/40
See application file for complete search history.

(56) References Cited

U.S. PATENT DOCUMENTS

| | | | |
|---|---|---|---|
| 6,349,824 | B1 | 2/2002 | Yamada |
| 6,634,494 | B1 | 10/2003 | Derr et al. |
| 7,011,213 | B2 | 3/2006 | Clark et al. |
| 11,730,555 | B2 | 8/2023 | Hendrix et al. |
| 2005/0092635 | A1 | 5/2005 | Jones et al. |
| 2010/0200002 | A1 | 8/2010 | Orban, III et al. |
| 2011/0017634 | A1 | 1/2011 | Sweeney |
| 2015/0047647 | A1 | 2/2015 | Winer |
| 2021/0113185 | A1 | 4/2021 | Nix et al. |
| 2021/0378763 | A1 | 12/2021 | Bailey et al. |
| 2022/0265245 | A1 | 8/2022 | Sowards et al. |

FOREIGN PATENT DOCUMENTS

| | | | |
|---|---|---|---|
| EP | 2957250 | B1 | 11/2020 |
| WO | 2008060947 | A2 | 5/2008 |
| WO | 2020223081 | A1 | 11/2020 |

OTHER PUBLICATIONS

Notification, Search Report, and Written Opinion from PCT Application No. PCT/IB2025/055813, dated Sep. 11, 2025, pp. 1-11.

(Continued)

*Primary Examiner* — Lawrence D Ferguson
(74) *Attorney, Agent, or Firm* — Paradice & Li LLP

(57) ABSTRACT

Systems, devices, and methods provide a sterile drape for a medical implement, such as a control device, to be used within a sterile field during a medical or surgical procedure. The sterile drape can be used to drape or wrap any of various medical implements or instruments in a manner so as to manage aseptic presentation of the instruments within the sterile surgical field. The use of the disclosed systems, devices, and methods can reduce contamination as well as maintain or enhance the usability of the instruments within the surgical field.

20 Claims, 11 Drawing Sheets

(56) References Cited

OTHER PUBLICATIONS

EXtremeRate, retrieved from website Dec. 9, 2024, https://extremerate.com/products/clear-full-set-housing-shell-with-buttons-touchpad-cover-for-ps5-controller-custom-replacement-decorative-trim-shell-front-back-plates-for-ps5-controller-qpfm5001, pp. 1-14.
EXtremeRate, retrieved from website Dec. 9, 2024, https://extremerate.com/products/replacement-full-set-shells-with-buttons-compatible-with-ps5-edge-controller-clear?_pos=11&_sid=b6e33feb9&_ss=r, pp. 1-20.
EXtremeRate, retrieved from website Dec. 9, 2024, https://www.amazon.com.au/eXtremeRate-Transparent-Controller-Housing-Replacement/dp/B08NPGRJH2?th=1, pp. 1-7.
EXtremeRate, retrieved from website on Jan. 31, 2024, https://wholesale.extremerate.com/products/clear-full-set-shell-kits-for-ps5-controller-bdm-030-040-050, 4 pages.

STERILE DRAPE

BACKGROUND

Field

The present disclosure relates generally to systems and methods for providing a sterile drape for medical instruments, such as control devices used in medical procedures.

Description of Related Art

Medical procedures such as endoscopy (e.g., bronchoscopy, colonoscopy, thoracoscopy, etc.) may involve accessing and visualizing the inside of a patient's lumen, hollow organs, or other body cavities for diagnostic and/or therapeutic purposes. During a procedure, a flexible tubular tool or instrument, such as an endoscope, may be inserted into the patient's body. In some instances, a second instrument can be passed through the endoscope to a tissue site identified for diagnosis and/or treatment.

In some medical procedures, human operator-controlled or robotically-enabled/assisted systems may be used to control the insertion and/or manipulation of the instruments used. The human operator-controlled or robotically-enabled medical system may include a user-operated control device used to control the positioning of the instrument during the procedures. Since the user-operated control device (and ancillary components) are within a sterile field during use, it is desirable that the control device and ancillary components maintain the sterility of the surgical site.

SUMMARY

A sterile drape can provide a sterile barrier for a medical implement, such as a control device used within a sterile field during a medical or surgical procedure. The control device may be used by the operator to perform a variety of procedures with equipment associated with the medical or surgical procedure, and may include a number of input controls as well as indicators. In an example, during such procedures, a physician can guide an instrument through a portion of a patient's body using the input controls of the control device. The indicators can provide feedback to the physician during the procedure. The sterile drape can provide a sterile barrier for the implement, while maintaining or enhancing the usability of the implement.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

1. Overview

Figure 1:
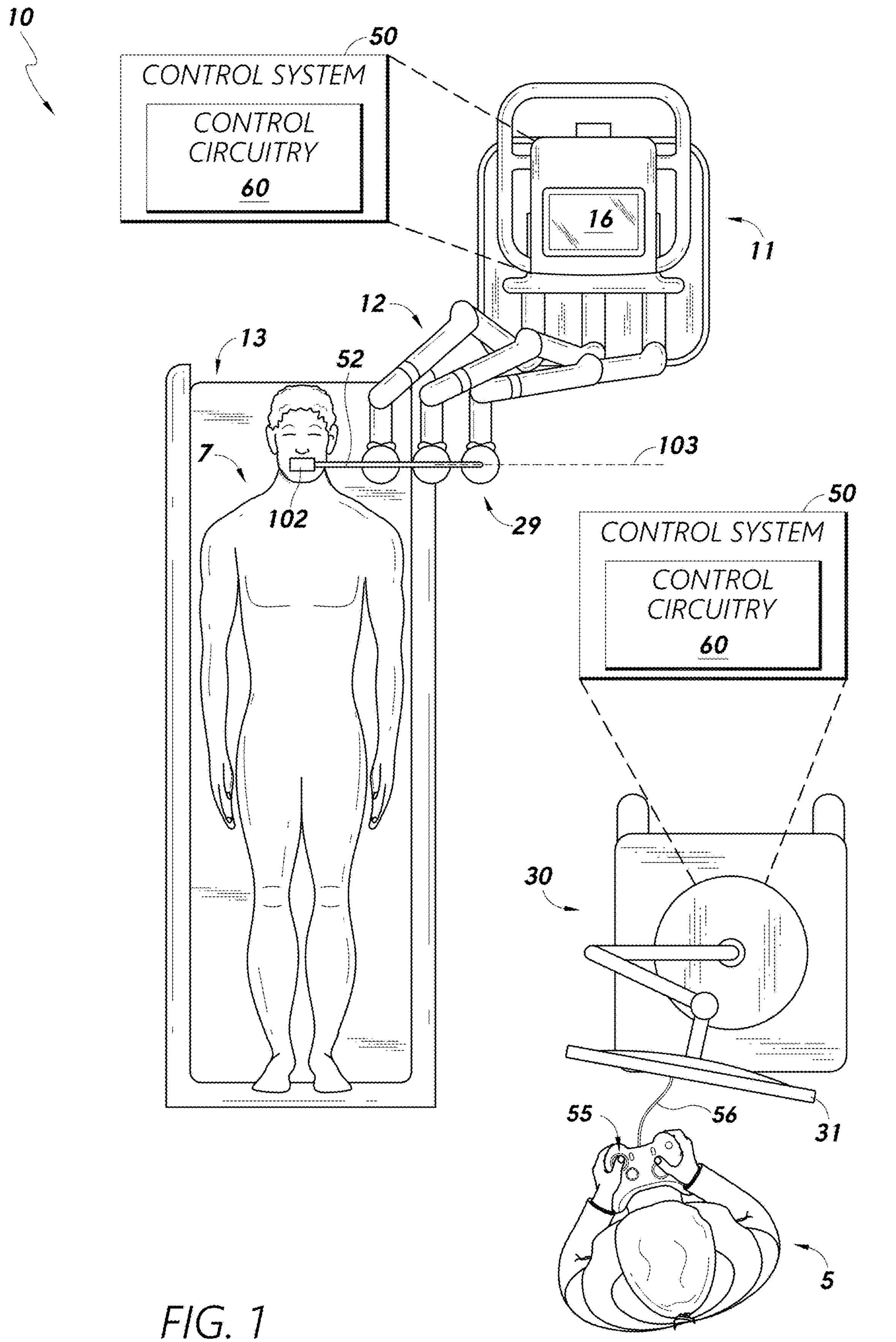
FIG. 1 illustrates an embodiment of a cart-based robotic system arranged for diagnostic and/or therapeutic endoscopy procedure(s).

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Aspects of the present disclosure may be integrated into a user-operated, robotically-enabled medical system capable of performing a variety of medical procedures, including laparoscopy, endoscopy, and various other procedures utilizing a control interface. Among endoscopy procedures, the system may be capable of performing bronchoscopy, ureteroscopy, gastroenterology, etc.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

The terms “scope” and “endoscope” are used herein according to their broad and ordinary meanings, and may refer to any type of elongate medical instrument having image generating, viewing, and/or capturing functionality and configured to be introduced into any type of organ, cavity, lumen, chamber, or space of a body. For example, references herein to scopes or endoscopes may refer to a bronchoscope, ureteroscope, cystoscope, nephroscope, arthroscope, colonoscope, laparoscope, borescope, or the like. Scopes/endoscopes, in some instances, may comprise a rigid or flexible tube, and may be dimensioned to be passed within an outer sheath, catheter, introducer, or other lumen-type device, or may be used without such devices.

User-operated, robotic-assisted endoscopy procedures can be implemented in connection with various medical procedures, such as bronchial procedures, wherein robotic tools can enable a physician to perform endoscopic target access (e.g., bronchoscope) as well as treatment. However, movements of target anatomical features during operation can be problematic in cases where the operating physician relies on a fixed access target position. Advantageously, aspects of the present disclosure can relate to real-time target tracking/guidance in medical procedures, which may also be utilized by the operating physician to direct an endoscopic instrument (e.g., camera, needle, or other rigid tool) and/or to guide robotic instrumentation, such as by adjusting endoscope position and/or alignment in response to such real-time target-tracking information. Although aspects of the present disclosure are described herein for convenience in the context of bronchoscope-guided procedures, it should be understood that inventive aspects of the present disclosure may be implemented in any suitable or desirable type of percutaneous and/or endoscopic medical procedure, whether robotic or not.

Robotic System

Figure 2:
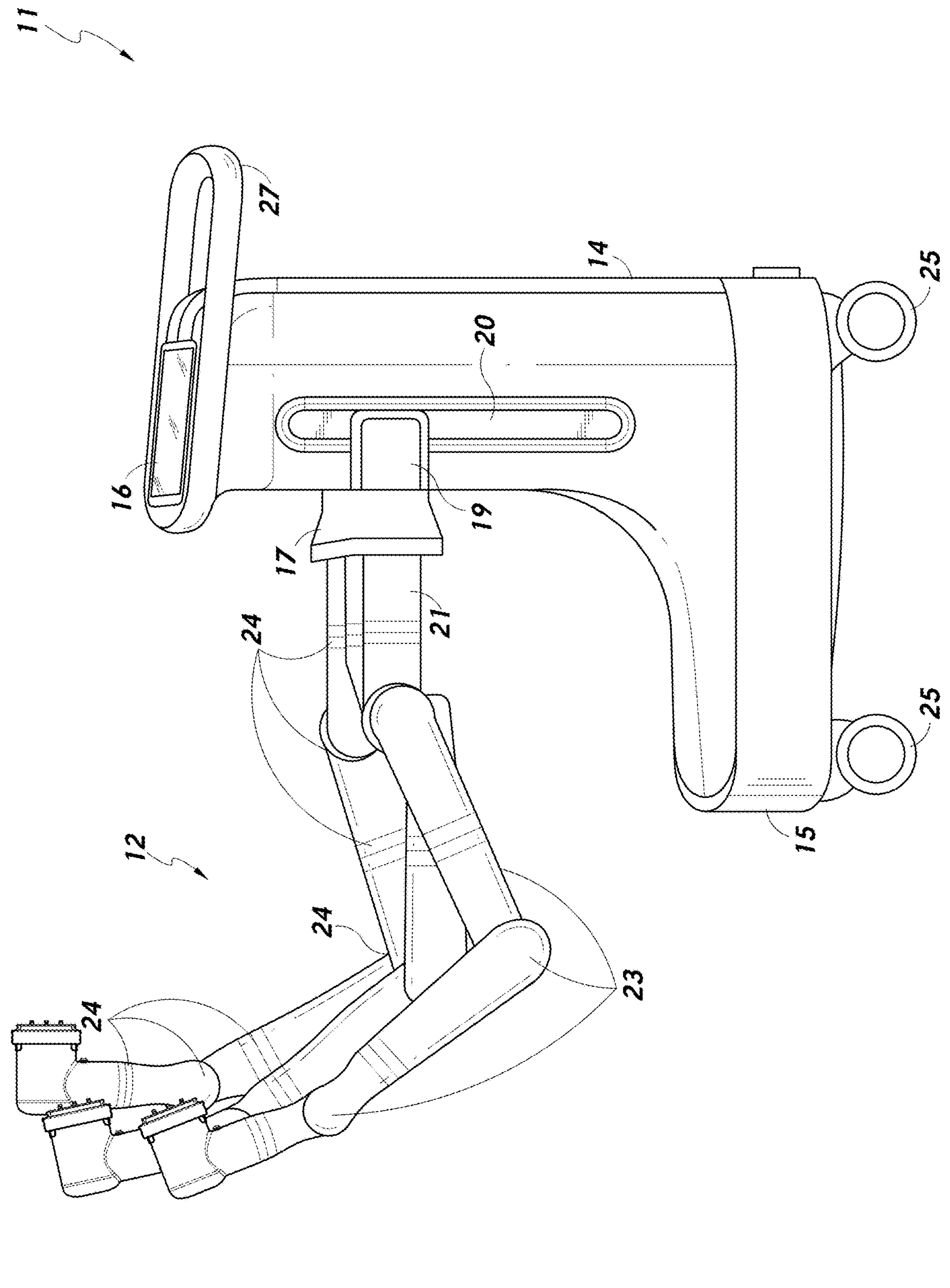
FIG. 2 depicts further aspects of the robotic system of FIG. 1.

The user-operated robotically-enabled medical system may be configured in a variety of ways depending on the particular procedure. FIG. 1 illustrates an embodiment of a cart-based robotically-enabled system 10 arranged for a diagnostic and/or therapeutic procedure. During an endoscopy, for example, the system 10 may comprise a cart 11 or table based system 36 (see FIG. 5) having one or more robotic arms 12 to deliver a medical instrument, such as a steerable endoscope 52 to a natural orifice access point (i.e., the mouth of the patient positioned on a table in the present example) to deliver diagnostic and/or therapeutic tools. As shown at FIG. 1, the cart 11 may be positioned proximate to the patient’s upper torso in order to provide access to the access point. Similarly, the robotic arms 12 may be actuated to position the endoscope relative to the access point. FIG. 2 depicts an example embodiment of the cart in greater detail.

With continued reference to FIG. 1, once the cart 11 is properly positioned, the robotic arms 12 may insert the steerable endoscope 52 into the patient robotically, manually, or a combination thereof in response to commands from a control device 55, for example. As shown, the steerable endoscope 52 may comprise at least two telescoping parts, such as an inner leader portion and an outer sheath portion, each portion coupled to a separate instrument driver 86 from the set of instrument drivers, each instrument driver 86 coupled to the distal end of an individual robotic arm 12. This linear arrangement of the instrument drivers 86, which facilitates coaxially aligning the leader portion with the sheath portion, creates a “virtual rail” 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 86 along the virtual rail 29 telescopes the inner leader portion relative to the outer sheath portion or advances or retracts the endoscope 52 from the patient. The angle of the virtual rail 29 may be adjusted, translated, and pivoted based on clinical application or physician preference.

The endoscope 52 may be directed down the patient’s trachea and lungs, for example, after insertion using commands from the control device 55 until reaching the target destination or operative site. In order to enhance navigation through the patient’s body and/or reach the desired target, the endoscope 52 may be manipulated to telescopically extend the inner leader portion from the outer sheath portion to obtain enhanced articulation and greater bend radius. The use of separate instrument drivers 86 also allows the leader portion and sheath portion to be driven independent of each other.

The system 10 may also include a movable tower 30, which may be connected via support cables to the cart 11 to provide support for controls, electronics, fluidics, optics, sensors, and/or power to the cart 11. For example, the control device 55 can be coupled to components at the tower 30 via wireless coupling or with wires/cables 56, or similar. Placing such functionality in the tower 30 allows for a smaller form factor cart 11 that may be more easily adjusted and/or re-positioned by an operating physician 5 and his/her staff. Additionally, the division of functionality between the cart 11 and the support tower 30 reduces operating room clutter and facilitates improving clinical workflow.

In support of the robotic systems described above, the tower 30 may include component(s) of a computer-based control system 50 that stores computer program instructions, for example, within a non-transitory computer-readable storage medium such as a persistent magnetic storage drive, solid state drive, etc. The control device 55 may be configured to send instructions to the computer-based control system 50, based on inputs from the operating physician 5. The execution of those instructions, whether the execution occurs in the tower 30 or the cart 11, may control the entire system or sub-system(s) thereof. For example, the operating physician 5 may activate various inputs on the control device 55, which sends instructions to the control system 50. When the instructions are executed by a processor of the control system 50, the instructions may cause the components of the robotics system 10 to actuate the relevant carriages and arm mounts, actuate the robotics arms, and control the medical instruments. For example, in response to receiving control signals from the control device 55, the motors in the joints of the robotics arms 12 may position the arms 12 into a certain posture.

The tower 30 may also include a pump, flow meter, valve control, and/or fluid access in order to provide controlled irrigation and aspiration capabilities that may be deployed through the endoscope 52. These components may also be controlled using the control system 50 via the control device 55. In some embodiments, irrigation and aspiration capabilities may be delivered directly to the endoscope 52 through separate cable(s).

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system 50, such opto-electronics equipment may be used to generate real-time data and/or images for display in any number of consoles deployed throughout the system, including in the tower 30. Data can also be displayed on one or more areas of the control device 55.

The tower 30 may also include a console 31 in addition to the control device 55 and any other consoles available in the rest of the system. The console 31 may include a user interface and one or more display screens ("displays" or "display devices"), such as a touchscreen, for the physician operator. The displays may include electronic monitors (e.g., LCD displays, LED displays, touch-sensitive displays), virtual reality viewing devices (e.g., goggles or glasses), and/or other display devices. In some embodiments, one or more of the displays provides position information about the instrument, such as indicated on the control device 55.

Display device(s) may be integrated with the user controls, for example, as a tablet device with a touchscreen or a touchscreen portion of the control device 55, providing for user input. The display device(s) can be configured to provide data and input commands to the robotic system 10 using integrated display touch controls. The display device (s) can be configured to display graphical user interfaces showing information about the position and orientation of various instruments operating within the patient and/or system based on information provided by one or more position sensors. In some embodiments, position sensors associated with medical instruments (e.g., an endoscope 52) may be configured to generate signals indicative of position and transmit the same on wires and/or transmitters coupled to the sensors. Such connectivity components may be configured to transmit the position information to the console base for processing thereof by the control circuitry 60 and for presentation via the display device(s).

Consoles and the control device 55 are generally designed to provide both robotic controls as well as pre-operative and real-time information of the procedure, such as navigational and localization information of the endoscope 52. The operator may provide inputs for controlling the robotic system 10 at the control device 55, for example, to navigate or guide the instrument to an area of interest. When an additional console 31 is available, it may be used by a second operator, such as a nurse, to monitor the health or vitals of the patient and the operation of system, as well as provide procedure-specific data, such as navigational and localization information. The console 31 may be embodied in a wide variety of arrangements or configurations. In the illustrated example, the console 31 includes a console base, displays (e.g., monitors), and one or more I/O devices (e.g., keyboard, joystick, etc.). As shown, the console 31 can also include the control device 55. A user (e.g., the operator or physician) can remotely control the medical robotic system 10 (e.g., the systems described with reference to FIGS. 1-13) from a convenient position using the control device 55 and/or other console components.

The control device 55 comprises a user-operated controller with multiple input controls available to the user. The input controls can include one or more joysticks, toggles, buttons, switches, knobs, touch pads, and the like. When operated, the input controls send control signals or control instructions to the control system 50 to cause the components of the robotics system 10 to actuate the relevant carriages and arm mounts, actuate the robotics arms, and activate separate instrument drivers 86 to control the medical instruments. The input controls on the control device 55 can include coarse and fine adjustments for precise movement of the instruments. The control device 55 can also include a plurality of read-outs, displays, indicators, and the like for visual and/or auditory feedback. Additionally, haptic feedback may also be available at the control device 55 for further indication. For example, haptic feedback may be used to indicate that preset limits are approached or breached.

The control device 55 may be coupled to the tower 30 or the cart 11 through one or more cables 56 or connections. Alternately, the control device 55 may be coupled to the tower 30 or the cart 11 wirelessly. The tower 30 may be coupled to the cart 11 and endoscope 52 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

The column 14 may internally comprise mechanisms, such as gears and motors that are designed to use a vertically aligned lead screw to translate the carriage 17 in a mechanized fashion in response to control signals generated in response to user inputs, e.g., inputs from the console 16 or the control device 55.

The robotic arms 12 may generally comprise robotic arm bases 21 and end effectors (e.g., instrument driver) 75, separated by a series of linkages 23 that are connected by a series of joints 24, each joint comprising an independent actuator, each actuator comprising an independently controllable motor. Each independently controllable joint 24 represents an independent degree of freedom available to the robotic arm. Each of the arms 12 have seven joints 24, and thus provide seven degrees of freedom. A multitude of joints 24 result in a multitude of degrees of freedom, allowing for "redundant" degrees of freedom. Redundant degrees of freedom allow the robotic arms 12 to position their respective end effectors 75 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen) to provide the physician user with both pre-operative and intra-operative data. Potential pre-operative data on the touchscreen may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite carriage 17. From this position the physician 5 may view the console 16, robotic arms 12, and patient while operating the console 16 from behind the cart 11. As shown, the console 16 also includes a handle 27 to assist with maneuvering and stabilizing cart 11.

Figure 3:
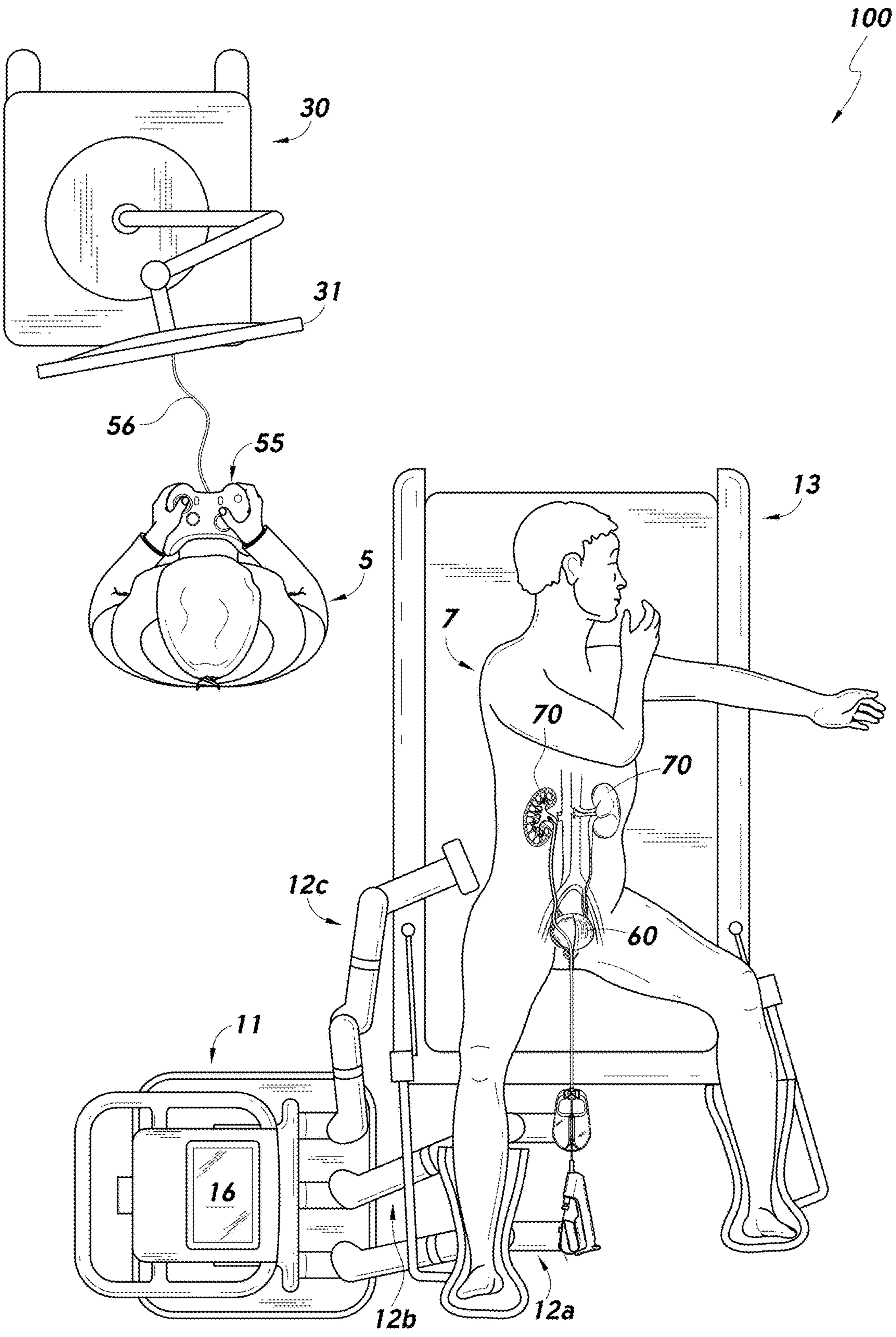
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope, a procedure-specific endoscope 52 designed to traverse a patient's urethra and ureter, to the lower abdominal area of the patient. In a ureteroscopy, it may be desirable for the ureteroscope to be directly aligned with the patient's urethra to reduce friction and forces on the sensitive anatomy in the area. As shown, the cart 11 may be aligned at the foot of the table 13 to allow the robotic arms 12 to position the ureteroscope for direct linear access to the patient's urethra.

From the foot of the table 13, the robotic arms 12 may insert ureteroscope along the virtual rail 29 directly into the patient's lower abdomen through the urethra, via control instructions initiated at the control device 55. After insertion into the urethra, the physician user can operate the control device 55, and using similar control techniques as in bronchoscopy, navigate the ureteroscope into the bladder 60, ureters, and/or kidneys 70 for diagnostic and/or therapeutic applications.

Figure 4:
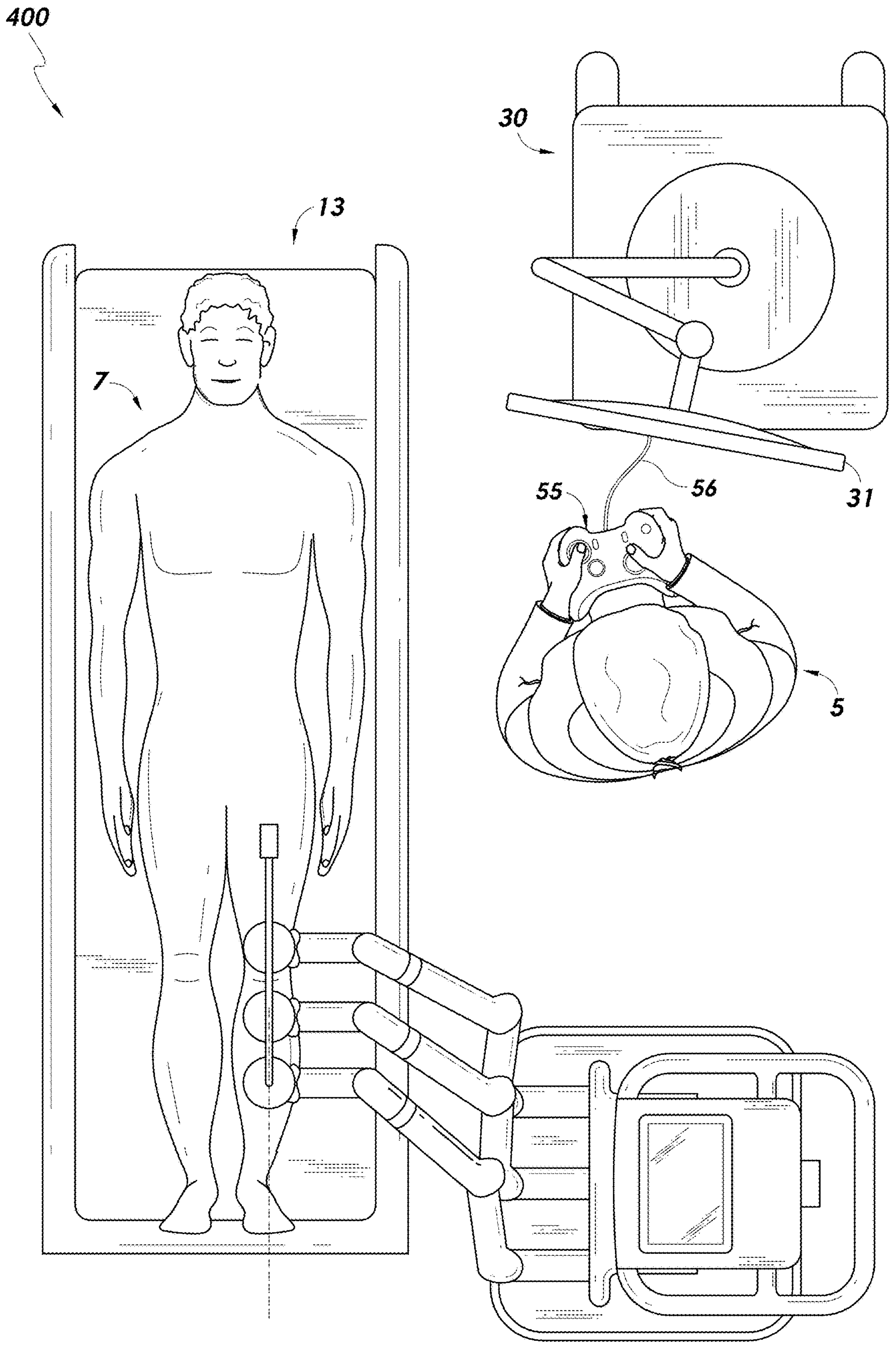
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg, via control instructions initiated at the control device 55. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 29 with direct linear access to the femoral artery access point in the patient's thigh/hip region. After insertion into the artery, the medical instrument 34 may be directed and inserted by translating the instrument drivers 86 via control instructions responsive to operator inputs at the control device 55. Alternatively, the cart 11 may be positioned around the patient's upper abdomen in order to reach alternative vascular access points, such as, for example, the carotid and brachial arteries near the shoulder and wrist.

Figure 5:
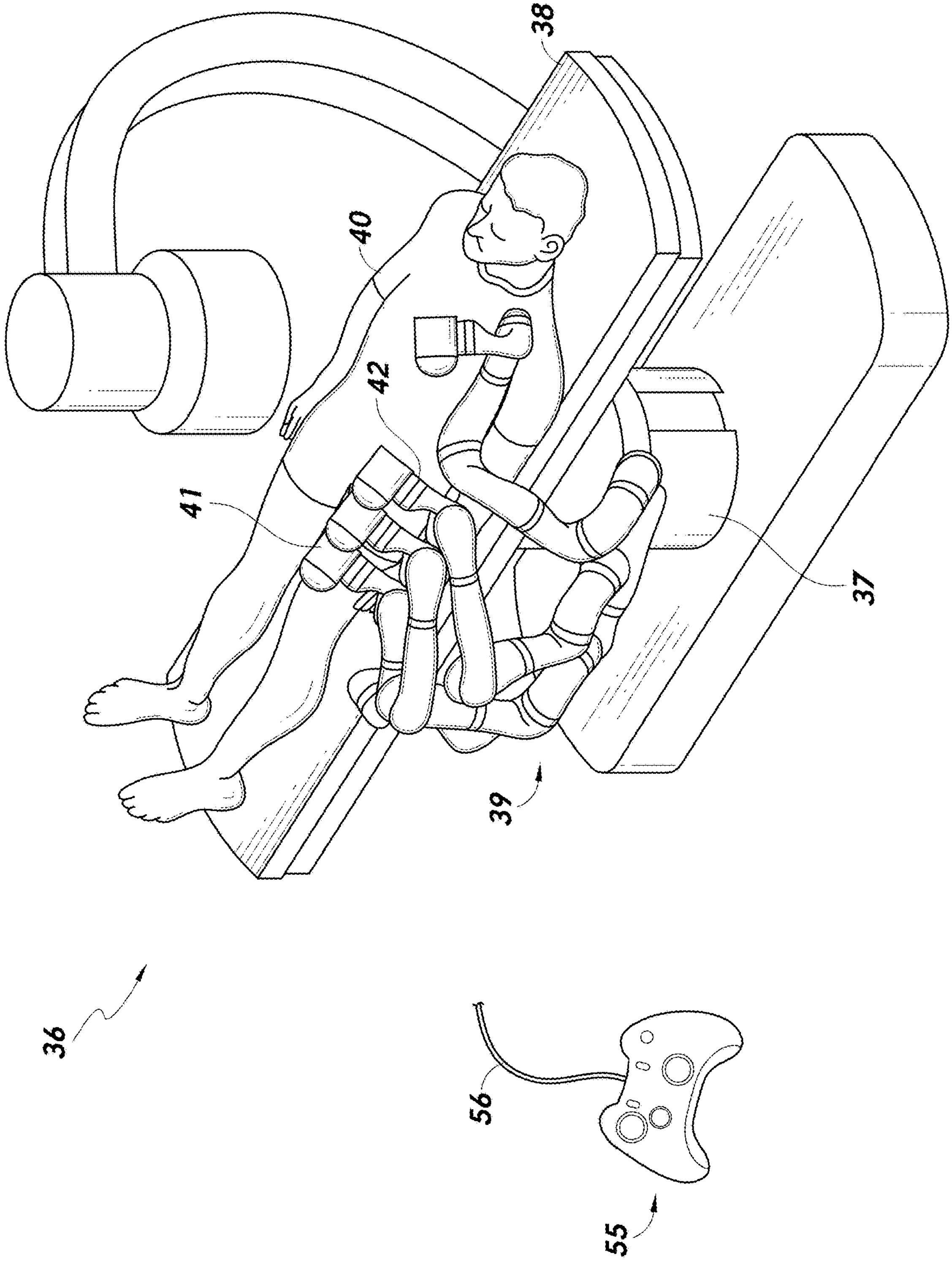
FIG. 5 illustrates an embodiment of a table-based robotic system arranged for an endoscopy procedure.

Embodiments of the robotically-enabled medical system 10 may also incorporate the patient's table 13. Incorporation of the table 13 reduces the amount of capital equipment within the operating room by removing the cart 11, which allows greater access to the patient. FIG. 5 illustrates an embodiment of such a robotically-enabled system 36 arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope through or along a virtual rail 41 formed from the linear alignment of the instrument drivers 42. The robotic arms 39 may insert a steerable endoscope into the patient robotically, manually, or a combination thereof in response to commands from a control device 55, for example. The system 36 may also include a movable tower 30, as discussed above, which may be connected via support cables to the platform 38 to provide support for controls, electronics, fluidics, optics, sensors, and/or power to the system 36, including support for the control device 55.

Figure 6:
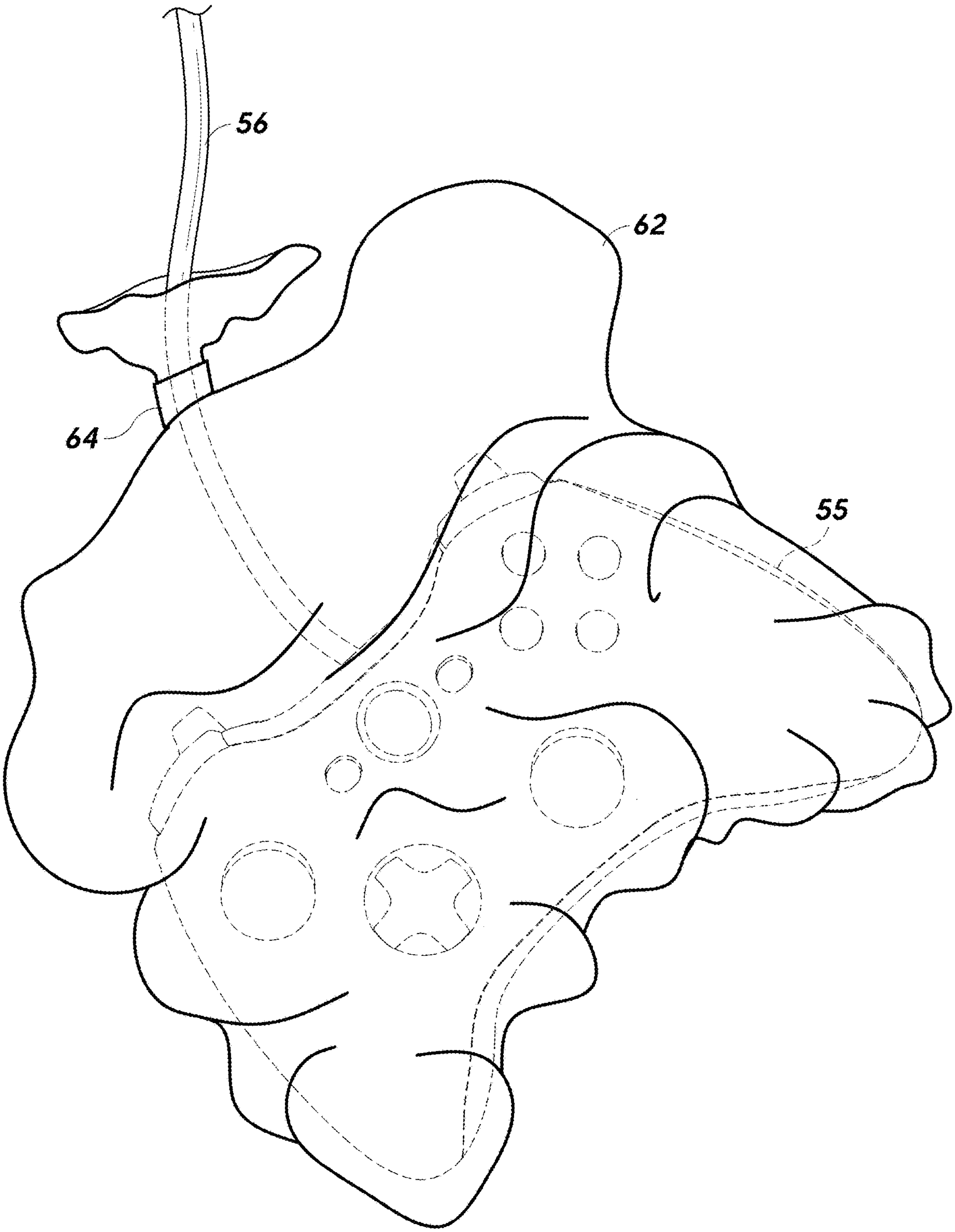
FIG. 6 depicts a control device wrapped in a sterile plastic sheet.

With the introduction of various electro-mechanical devices and systems of the robotically-enabled medical system 10 into the sterile field of the operating room, it is desirable to preserve the sterility of the operating environment notwithstanding the presence of the equipment. In some configurations, plastic sheets, or the like, may be disposed on or around portions of the various devices and systems to provide sterile barriers. For example, plastic sheets can be wrapped around the cart 11, portions of the robotic arms 12, the tower 30, and various surfaces to be interacted with. As illustrated at FIG. 6, a plastic sheet 62 can also be wrapped around the control device 55 as a sterile wrapping. A twist tie or tape 64 can be used to close the plastic sheet 62 around the device 55. The use of the plastic sheet 62 may provide a sterile barrier between the particular equipment and the surgical field, thereby allowing for the use of a robotic system 10 in the sterile surgical field. Additionally, some components of the system 10 may be configured to be coupled to various types of sterile adapters that may be coupled to sterile instruments intended to interact directly with the patient, such as the endoscope 52. With the equipment covered in plastic, the physician and/or other technician(s) may interact with various components of the robotic cart 11, the tower 30 (e.g., a touchscreen), or with the control device 55 during a surgical procedure. Plastic barriers may further protect against equipment biohazard contamination and/or minimize clean-up after a procedure.

However, the use of a plastic sheet 62 (or the like) as a sterile barrier can negatively impact the usability of some devices, such as the control device 55, for example. For instance, the plastic sheet 62 can make the control device 55 more difficult to hold steadily, or to grasp, since the plastic sheet 62 can have a slippery effect. There can also be an on-going need to re-adjust the plastic sheet 62 on the control device 55 as it moves on and over the device 55 during use or handling. In some cases, the legends on the control device 55 can be harder to read or to read accurately through the plastic sheet 62. Indicators, including read-outs or measurements on the control device 55 can also be harder to read well through the plastic sheet 62, which can cause distortion. In many cases, the physician operator 5 is required to take additional time or effort to read or clearly see displayed information.

Additionally, the plastic sheet 62 can make it more difficult to move input controls on the control device 55 with precision. The plastic sheet 62 may cause the operator's hands to slide over control surfaces rather than making a positive grip or contact with the controls. Further, the plastic sheet 62 can potentially restrict full movement of some of the input controls. For example, the plastic sheet 62 can restrict a joystick from moving in all directions without hindering the movements. In some examples, moving one input control on the control device 55 through the plastic sheet 62 can cause the plastic sheet 62 to pull or push on one or more other controls on the control device 55, resulting in unintended movement of the surgical apparatus or operation of equipment. In other examples, the presence of the plastic sheet 62 can hinder the efficient operation of the input controls or other parts of the control device 55.

2. Conforming Sterile Drape

Due to the rigorous environmental conditions typically associated with a sterile surgical field, introducing certain types of equipment into the surgical field can present challenges to maintaining the environment. The systems, devices, and methods disclosed herein are suitable and can be advantageously employed within the sterile surgical field. As disclosed with various examples, the systems, devices, and methods disclosed herein can be used to drape or wrap any of various medical implements or instruments in a manner so as to manage aseptic presentation of the instruments within the sterile surgical field. The use of the disclosed systems, devices, and methods can reduce contamination as well as maintain or enhance the usability of the instruments within the surgical field.

The disclosed concepts may be adapted to any application where the desire for sterile barrier management and optimized usability are regarded. Additionally, the disclosed concepts may also be applied to any application where a single implement or multiple implements are coupled to at least one other component, and where each of the implements/components is to be sterilely interfaced. For instance, the disclosed concepts, devices, and techniques can be used with a system that includes a controller for controlling robotic components. The present disclosure includes a sterile drape for encasing the controller, and alternately some associated components of the controller (such as cables, cords, wires, etc.).

A novel sterile drape design is disclosed for wrapping/draping/encasing one or more implements/components in a sterile barrier. The shape of the sterile drape is configured to conform to the outer surface of an identified implement/component, providing a snug fit around the implement so as to maintain or enhance usability of the implement in a medical or surgical application. Maintaining or enhancing usability can include improving handling or gripping of the implement, full and unimpeded operation of any controls of the implement, clearly reading any legends or indicators on the implement or its controls, clearly reading any displays of the implement, clearly hearing any auditory indicators or feeling any haptic indicators of the implement, and so forth.

Certain examples are disclosed herein in the context of medical or surgical implements, instruments, devices, systems, components, tools, and the like. Examples of a control device 55 and associated components for a robotically-enabled medical system 10 are illustrated. However, although certain principles disclosed herein may be particularly applicable to such implements and components, it should be understood that the systems, devices, and methods of the present disclosure may be used to sterilely drape or wrap any suitable or desirable instruments, implements, tools, components, and the like. Furthermore, examples of the present disclosure may be utilized with items in non-biological environments as well.

As referenced above, the disclosed techniques, devices, and systems relate to sterile barriers, and specifically to a sterile drape which can be advantageously used for wrapping or draping surgical implements or other items intended to be used in a sterile surgical field, for example. Disclosed embodiments include an example sterile drape 102 that can be formed to enclose a single item or multiple items as desired. The disclosed concepts may be adapted to various applications, including where the desire for sterile barrier management and optimized usability are regarded.

Referring to FIGS. 7-13, an example sterile drape 102 for sterilely wrapping or draping one or more implements (e.g., medical implements, etc.) is illustrated. Each sterile drape 102 comprises at least a first sheet 104 and a second sheet 106. The first sheet 104 includes a first part 108 of the first sheet 104 having first contours 112 configured to conform to a first surface of the implement to be wrapped and a second part 110 of the first sheet 104 comprising a planar extension 114 of the first part 108 of the first sheet 104. The second sheet 106 includes a first part 118 of the second sheet 106 having second contours 122 configured to conform to a second surface of the implement to be wrapped and a second part 120 of the second sheet 106 comprising a planar extension 124 of the first part 118 of the second sheet 106. The first sheet 104 and the second sheet 106 have substantially the same perimeter shape (e.g., matching perimeter shapes), which perimeters are aligned one to the other.

Each of the sheets 104 and 106 can be formed (e.g., thermoformed) to wrap or drape a single implement or component. For example, the first sheet 104 ("upper sheet") can be formed to conform to an "upper" surface of the implement and the second sheet 106 ("lower sheet") can be formed to conform to a "lower" surface of the implement. In some cases, the drape 102 can be formed to accept multiple implements, or may be formed to accept the single implement and its associated accompanying components. For instance, the drape 102 can be formed to wrap or drape the control device 55 and at least a portion of its cable(s) 56.

The first part 108 of the first sheet 104 and the first part 118 of the second sheet 106 are formed to include first contours 112 and second contours 122, respectively, such as depressions, protrusions, features, and so forth, in the shapes of the respective upper and lower surfaces of the implement and any controls thereon, so as to provide a snug fit while maintaining or enhancing usability. The contours 112 and 122 can cover over controls on the surfaces of the upper and lower surfaces of the implement while allowing the controls to be fully utilized. The sterile drape 102 is sterile or sterilized (or capable of sterilization) and is configured to provide a sterility of medical or surgical implements wrapped therein.

The first sheet 104 and the second sheet 106 of the drape 102 are each comprised of a formed sheet of material. However, the first sheet 104 and the second sheet 106 may each be comprised of a single layer of material or one or both may be comprised of multiple (e.g., laminated) layers of material. A thickness of each of the first sheet 104 and the second sheet 106 (which may be different thicknesses) is configured for minimizing added bulk to the implement and for optimal handling and operation of the controls of the implement. Both the first sheet 104 and the second sheet 106 have an inside surface that is intended to be in contact with the implement and an outside surface that is intended to be in contact with the environment. In some cases, the inside surface and the outside surface of one or both of first sheet 104 and the second sheet 106 have a different texture.

As shown at FIGS. 7-13, the first part 108 of the first sheet 104 includes one portion of a molded cavity 130 shaped to conform to the implement to be wrapped therein. The first part 118 of the second sheet 106 includes another portion of the molded cavity 130. The first part 108 of the first sheet 104 and the first part 118 of the second sheet 106 are aligned along respective common perimeters, and the cavity 130 is disposed between them. The cavity 130 substantially conforms to the outer shape and features of the implement to be wrapped therein, so that the implement fits snugly within the cavity 130. While the cavity 130 is generally configured to conform to a particular implement, in an alternate embodiment, a less specific cavity 130 can be formed to accommodate a range of implements.

As also shown at FIGS. 7-13, the second part 110 of the first sheet 104 comprises a planar extension 114 of the first part 108 of the first sheet 104, and the second part 120 of the second sheet 106 comprises a planar extension 124 of the first part 118 of the second sheet 106. The planar extension 114 and the planar extension 124 each extend from the contours 112 and 122, respectively, and thus the cavity 130. The second part 110 of the first sheet 104 and the second part 120 of the second sheet 106 are aligned along respective common perimeters, and sealed, forming an apron 132 extending laterally from the cavity 130. The apron 132 comprises a planar envelope of the drape 102 and includes an access to the cavity 130 at a proximal portion of the apron 132, as well as an interface 134 from the drape 102 to one or more additional sterile wraps or drapes within the sterile surgical field. In other words, the drape 102 can be interfaced (e.g., sealed) to another sterile wrap or drape to provide a continuous sterile barrier over and around medical equipment within the sterile surgical field, if desired. The interface 134 comprises an area at the distal extent of the apron 132. The apron 132 also provides a sterile barrier for cables or other accessories attached to the implement that is wrapped in the cavity 130.

As shown at FIGS. 7-13, the apron 132 can extend from a "back" side 142 of the cavity 130, where the "front" side 140 comprises a side of the cavity 130 that is gripped by the user while the implement is within the cavity 130, and the back side 142 comprises a side opposite the front side 140. As also shown, the apron 132 can optionally extend partially from the "left" side 144 of the cavity 130 and partially from the "right" side 146 of the cavity 130 to provide a wider apron 132. A wider apron 132 allows for a wider interface 134 to other sterile wraps or barriers in the sterile surgical field. The interface 134 can have a width WI that is greater than a width $W_C$ of the cavity 130.

The first sheet 104 is coupled to the second sheet 106 to form the drape 102. The first sheet 104 and the second sheet 106 are stacked with the perimeter of the second sheet 106 being aligned to the perimeter of the first sheet 104. For example, the perimeter of the second sheet 106 is at least substantially the same shape and size as the perimeter of the first sheet 104. In alternate embodiments, the perimeters may have some differences, with an overall similarity. A seal 136 extends along a first portion 152 of the perimeter of the first sheet 104 and along a corresponding first portion 162 of a perimeter of the second sheet 106, sealing the second sheet 106 to the first sheet 104 along the seal 136, and thereby forming the cavity 130 between the first part 108 of the first sheet 104 and the first part 118 of the second sheet 106, and forming the apron 132 between the second part 110 of the first sheet 104 and the second part 120 of the second sheet 106. The first portion 152 of the perimeter of the first sheet 104 extends from a first end 121 of a first edge 123 of the first sheet 104, across a front edge 133*a* of the cavity 130, and to a first end 125 of a second edge 127 of the first sheet 104. The first portion 162 of the perimeter of the second sheet 106 follows the corresponding edges on the second sheet 106. The first portion 152 of the perimeter of the first sheet 104 and the first portion 162 of the perimeter of the second sheet 106 are opposite the opening 138. The seal 136 couples the first edge 123 of the first sheet 104 to the first edge 143 of the second sheet 106, couples corresponding front edges 133*a* and 133*b* of the first 104 and second 106 sheets, respectively, and couples a second edge 127 of the first sheet 104 to a second edge 147 of the second sheet 106. In other words, the seal 136 couples the first sheet 104 to the second sheet 106 along each of the edges but one—at the opening 138. The seal 136 can be formed using a heated sealing device, a laser-based device, an ultrasound sealing device, or like device, that melts (or welds, etc.) the material of the first sheet 104 to the material of the second sheet 106. Alternately or additionally, adhesives or other substances that form a bond can be used to form the seal 136. The seal 136 can be formed to avoid extra material at an overlap of the first sheet 104 and the second sheet 106 by avoiding the overlap. For example, there may be no overlap of the first 104 and second 106 sheets at the seal 136.

Figure 10:
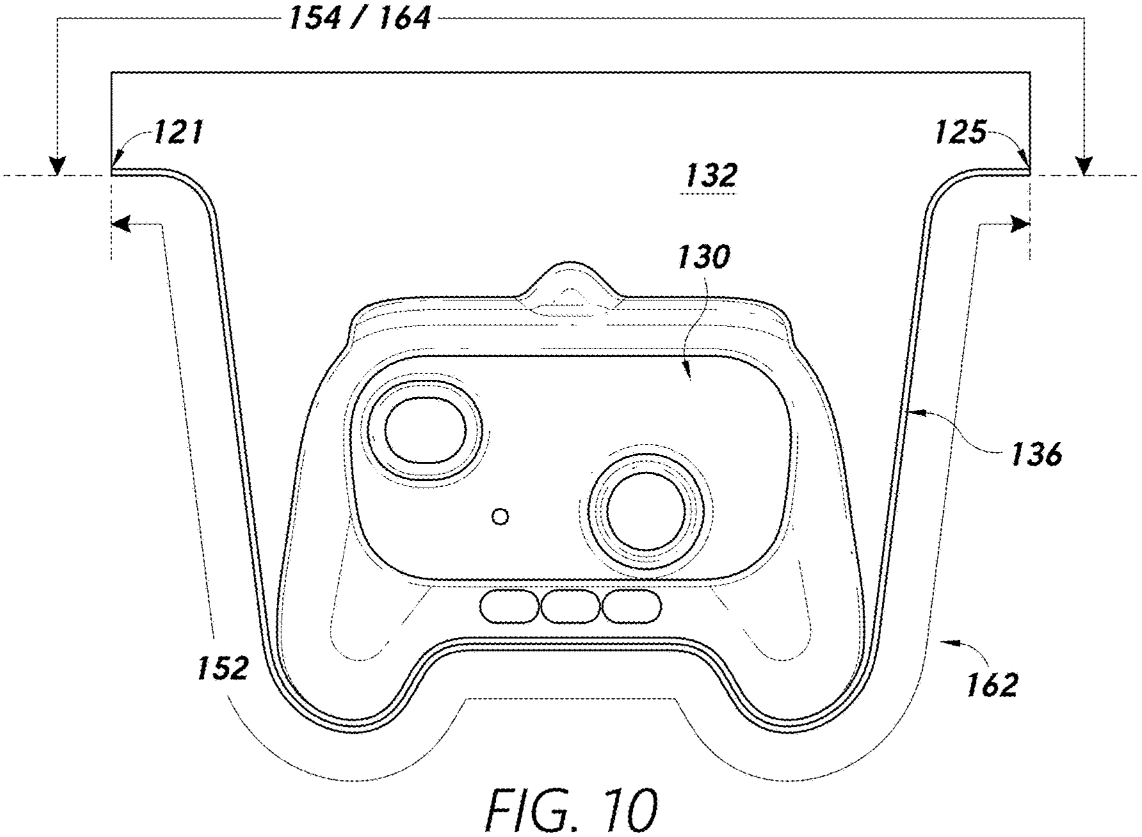
Figure 11:
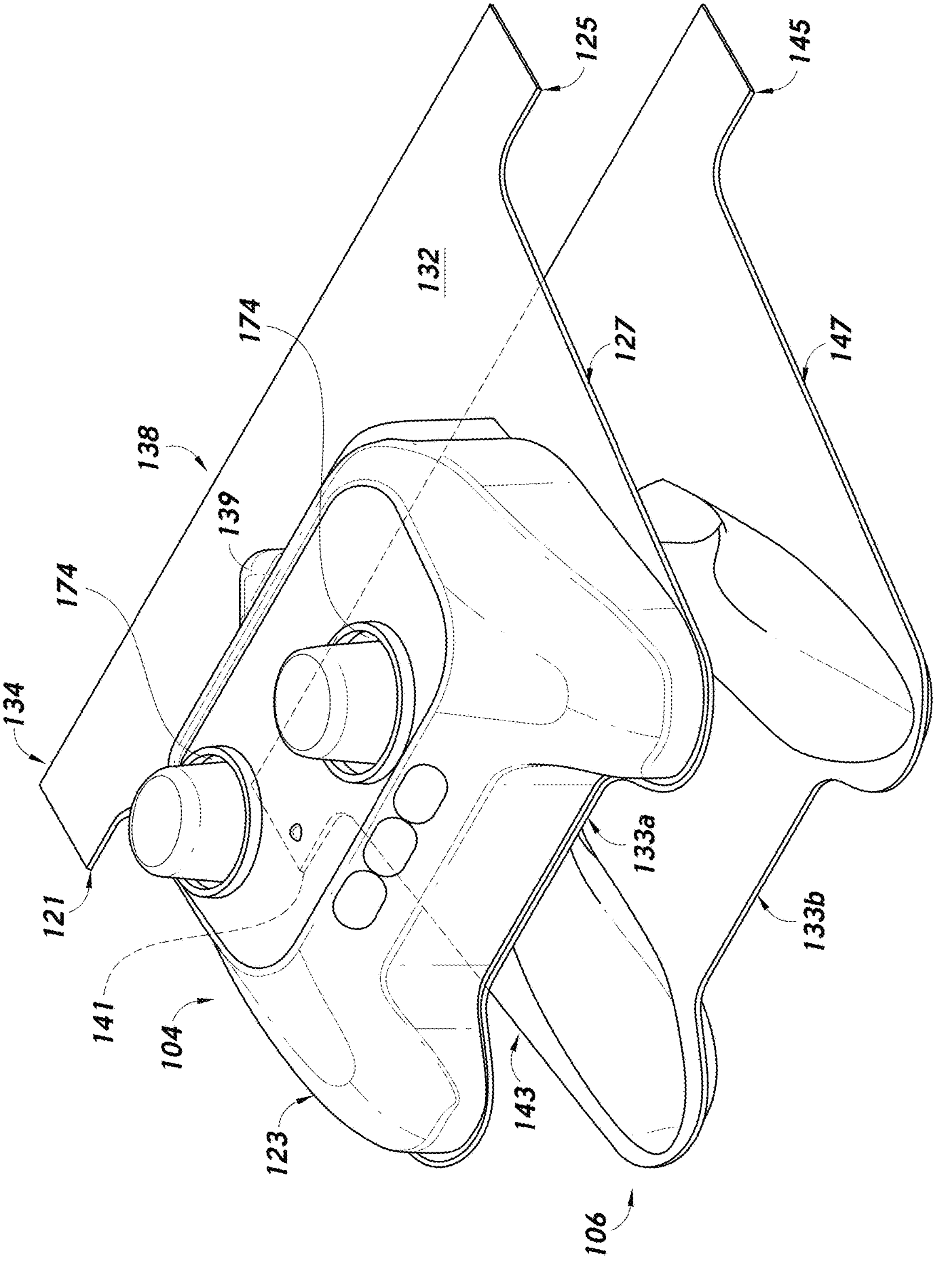

An opening 138 is disposed at a portion of the perimeter of the drape 102 where the seal 136 is not present. The opening 138 extends along a second portion 154 of the perimeter of the first sheet 104 and along a corresponding second portion 164 of the perimeter of the second sheet 106. For example, the opening 138 is disposed at a distal portion of the planar envelope (e.g., apron 132) and configured to provide access to the cavity 130 via the apron 132. Referring to FIGS. 10 and 11, the opening 138 extends from the first end 121 of the first edge 123 of the first sheet 104 and a first end 141 of the first edge 143 of the second sheet 106 to a first end 125 of the second edge 127 of the first sheet 104 and a first end 145 of the second edge 147 of the second sheet 106. The opening 138 comprises an access to the cavity 130, via the second part 110 of the first sheet 104 and the second part 120 of the second sheet 106. In other words, an implement can be wrapped or encased in the cavity 130 of the drape 102 by inserting the implement into the opening 138 and through the apron 132, and then into the cavity 130. Note that the material of the drape 102 has sufficient flexibility to move, bend, or flex as the implement is inserted through the planar envelope of the apron 132 and into the cavity 130. Note also that the first sheet 104 is sealed to the second sheet 106 along a front edge 133 of the cavity 130, without sealing side edges (e.g., sides) 144 and 146 or the back edge (e.g., side) 142 of the cavity 130. This allows the implement to be inserted into the cavity 130 and fitted to the front edge 133 of the cavity 130. The implement can stay snugly fitted to the front edge 133 of the cavity 130, with the drape 102 conforming to the shape of the implement. Once in the cavity 130, the implement can be adjusted in position to fit the conforming features, including the first contours 112 and second contours 122 of the first sheet 104 and the second sheet 106. Adjusting the position of the implement provides a snug fit of the implement within the cavity 130 of the drape 102. Once in position, the implement can be used in the sterile surgical field, with the drape 102 providing a sterile barrier around the implement.

Figure 7:
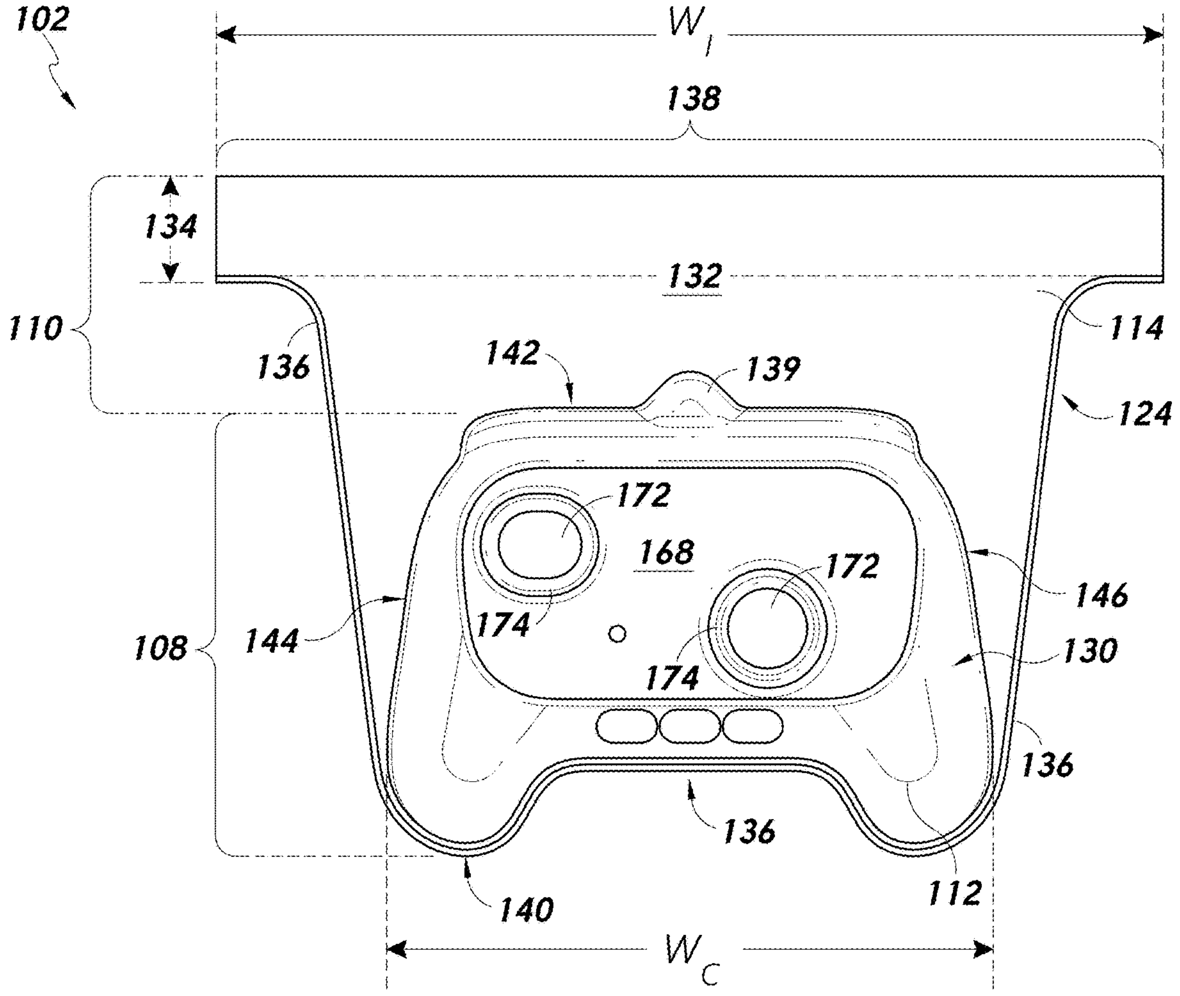
FIGS. 7-11 illustrate various views of an embodiment of a sterile drape for a control device.
Figure 8:
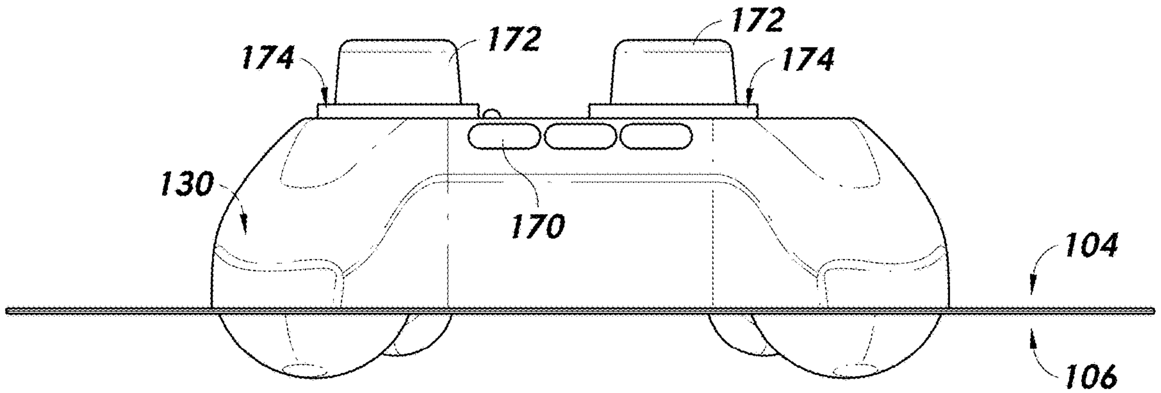
Figure 9:
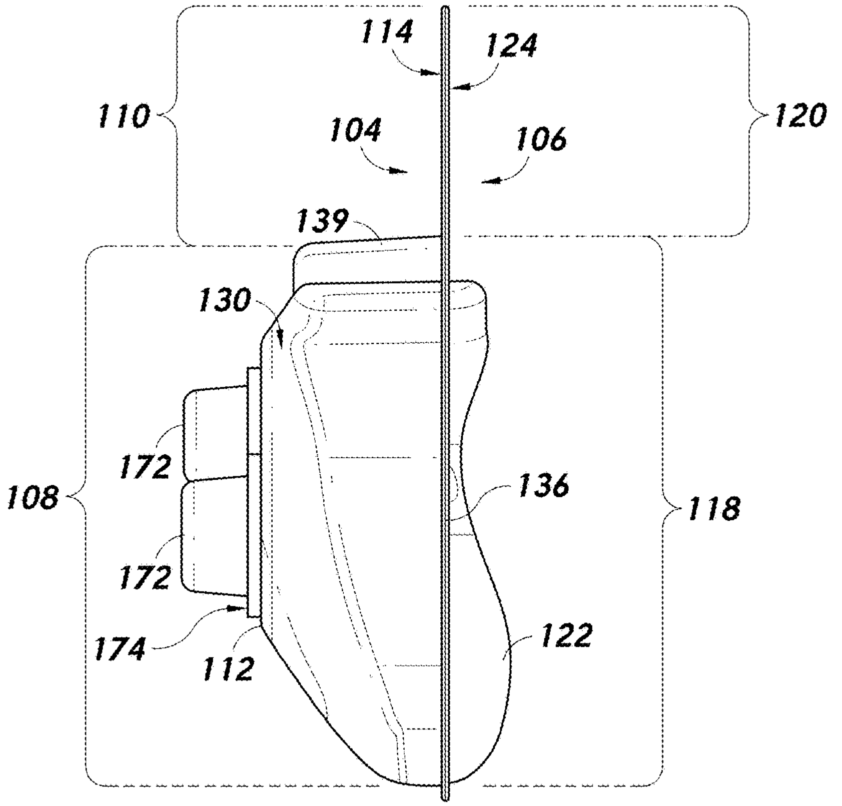

In various applications, the implement to be wrapped in the sterile drape 102 includes various input controls, such as joysticks, toggles, buttons, switches, knobs, touch pads, and the like. When operated, the input controls send control signals or control instructions to cause various components of a mechanically-enabled system, for example, to function in a precise manner. FIG. 8 illustrates a front view of an example sterile drape 102. As shown, the drape 102 can include one or more contours, reliefs, or features 170 configured to conform to a corresponding input control or indication component of the implement. The features 170 are raised to fit raised portions of the implement (e.g., raised input controls or indication components) and are recessed for recessed portions of the implement (e.g., recessed input controls or indication components), and so forth. This allows the drape 102 to snugly fit the implement, mimicking the shape of the implement, including the controls and indicators of the implement. As shown at FIG. 7 the drape 102 can include one or more tactile areas 168 on the first part 108 of the first sheet 104, configured to allow user-operation of touch-sensitive controls on the implement (e.g., controller). As also shown, the drape 102 can include a hollow protrusion 172 at the first part 108 of the first sheet 104, configured to receive and to conform to an input device of the implement, such as a joystick or the like. The hollow protrusion 172 encases and conforms to the input device to provide a sterile barrier for the input device. The hollow protrusion 172 can extend substantially normal to the first part 108 of the first sheet 104, and out of the first part 108 of the first sheet 104. Alternately, the hollow protrusion 172 can extend out of the first part 108 of the first sheet 104 at an angle or otherwise to conform to the input device of the implement. The hollow protrusion 172 fits snugly over the input device so that the input device can be operated by the user with the same precision as if the drape 102 was not present. In other words, the hollow protrusion 172 provides a sterile barrier for the input device of the implement without hindering the operation or full range of motion of the input device.

The drape 102 can include a trough 174 at a base of the hollow protrusion 172 and around a perimeter of the hollow protrusion 172. The trough 174 comprises slack material concentrated at the base of the hollow protrusion 172 and around some or all of the perimeter of the hollow protrusion 172. The slack material of the trough 174 provides a relief for movement of the hollow protrusion 172, so that the hollow protrusion 172 can move to a full extent without pulling on the material of the rest of the drape 102. For example, a joystick of the implement that is encased within the hollow protrusion 172 can be moved in any direction with the hollow protrusion 172 of the drape 102 in place, and moving the joystick will not pull on or put tension on any remaining portions of the drape 102. The slack material of the trough 174 is configured to become tauter or less slack in a first direction when the input device (e.g., joystick) is moved in an opposite direction, allowing the input device to be moved in the first direction without putting tension on a remainder of the first part 108 of the first sheet 104. This is important so that the input device can be operated to its full extent without the drape 102 hindering the movement of the input device, and also so that movement of the input device does not inadvertently move or activate another input control of the implement—or hinder the movement of any other input control due to tension on the drape 102. Accordingly, the trough 174 can include sufficient slack material (or extra slack material) to allow the input device full movement in all intended directions. In various applications, the slack material of the trough 174 can be folded in a plurality of concentric rings or otherwise be gathered in the trough 174 at the base of the hollow protrusion 172. The concentric rings or other gathering techniques can help to manage the slack material of the trough 174, including extra slack material in the direction that the input device (and the hollow protrusion 172) is moved. In applications where the implement includes more than one joystick type of input device (or the like), the drape 102 can include an equal number of hollow protrusions 172. Multiple hollow protrusions 172 are arranged on the drape 102 at locations corresponding to the input devices on the implement, and in the shape and size to conform to each of the input devices.

Figure 12:
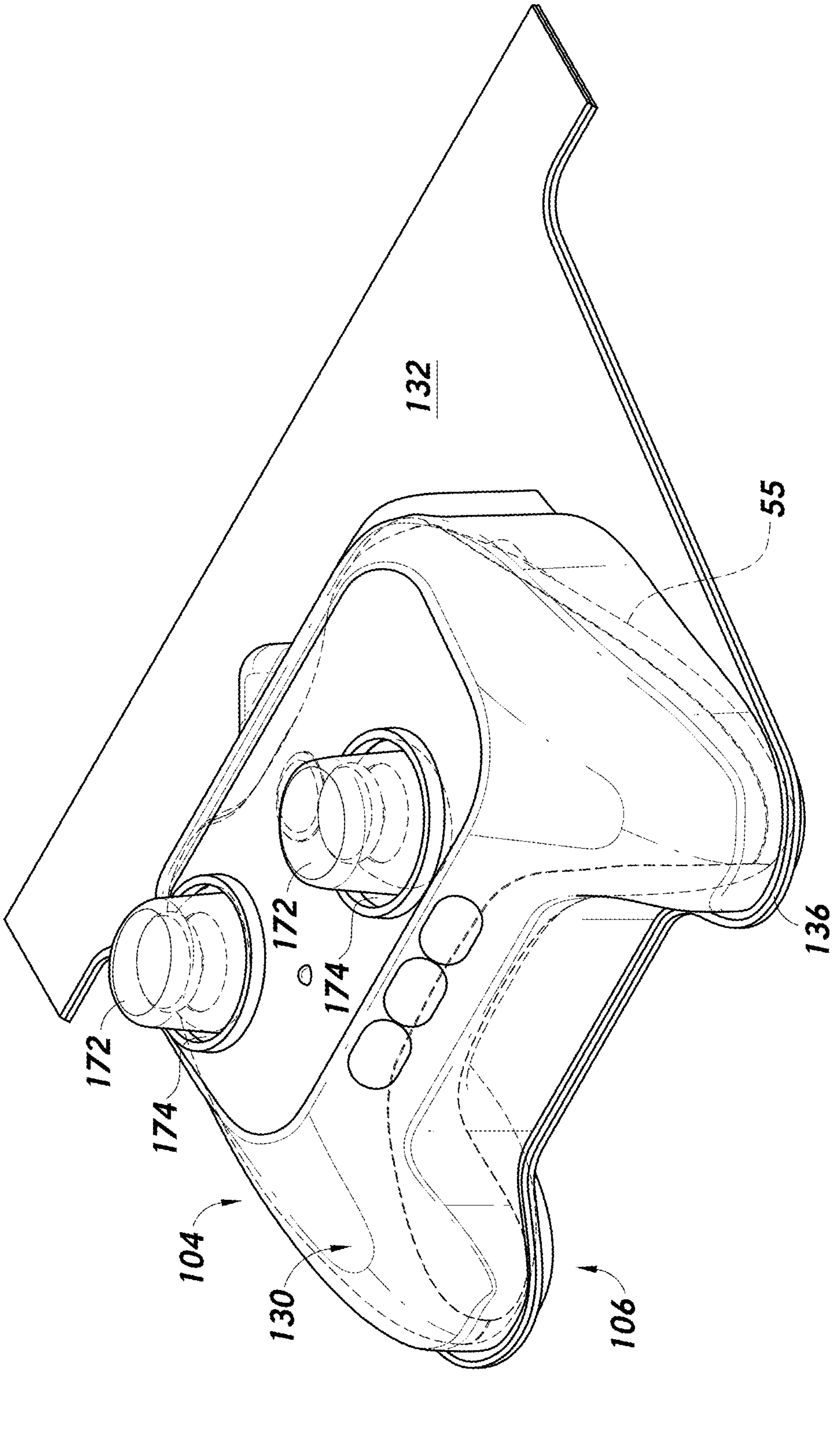
FIG. 12 illustrates a view of an example controller wrapped in an embodiment of a sterile drape.

Referring to FIG. 12, an example implement is shown wrapped (e.g., encased) in an example embodiment of a sterile drape 102. The implement shown represents a controller for a mechanically-enabled apparatus, for instance the robotic system 10, such as for an endoscopy system, or the like. Alternately, other implements can be wrapped in like manner, with the corresponding advantages. As shown at FIG. 12, the sterile drape 102 fits snugly around the implement, including around the contours and features of the implement and its input controls and indicators. The sterile drape 102 includes corresponding contours (112 and 122) and features 170 to mimic the shape of the implement as well as to conform to the input controls and indicators. The snug fit of the sterile drape 102 around the implement allows the implement to be operated by the user with as much ease and precision as if the sterile drape 102 was not installed. For example, the input controls of the implement (such as joysticks, toggles, buttons, switches, knobs, touch pads, and so forth) can be operated to their full extent and without hindrance or interfering with any other input controls or indicators. Operation of an input control does not pull on the remainder of the drape 102, outside of that portion of the drape 102 that is wrapped on the input control of interest. Additionally, the snug fit of the drape 102 and the materials used for the drape 102 provides that the tactile form, feel, and feedback of joysticks, controller buttons, etc. of the implement are consistent with or without the drape 102. Further, at least the first part 108 of the first sheet 104 is transparent to visible light. This may be accomplished by using a transparent material for the first sheet 104, or at least for the first part 108 of the first sheet 104. This provides visibility for the user to easily see and read legends on buttons or indicators, as well as on read-outs or displays, if present. In some cases, the entire drape 102 may be formed from a transparent material.

As shown at FIGS. 7-13, the drape 102 can include additional features to accommodate cords, cables, or other associated components of the implement. For example, the drape 102 can include a protruding notch 139 or bubble at the top sheet 104 to make room for a cord or cable attachment. The protruding cord notch 139 can extend out from the cavity 130 at the first part 108 of the first sheet 104 and may extend partly into the second part 110 of the first sheet 104. In some cases, the notch 139 can also extend into the second sheet 106. While the figures show the notch 139 protruding from a center portion at the distal end of the cavity 130 (e.g., back side 142), the notch 139 can also protrude from other portions of the cavity 130. The notch 139 allows the cavity 130 to snugly fit and closely conform to the implement while providing a relief for a cable attachment to the implement. The cable can then be covered by the apron 132 of the drape 102 to provide sterility for the cable. Some embodiments of a drape 102 can have more than one notch 139 to accommodate multiple cable attachments to an implement.

Figure 13:
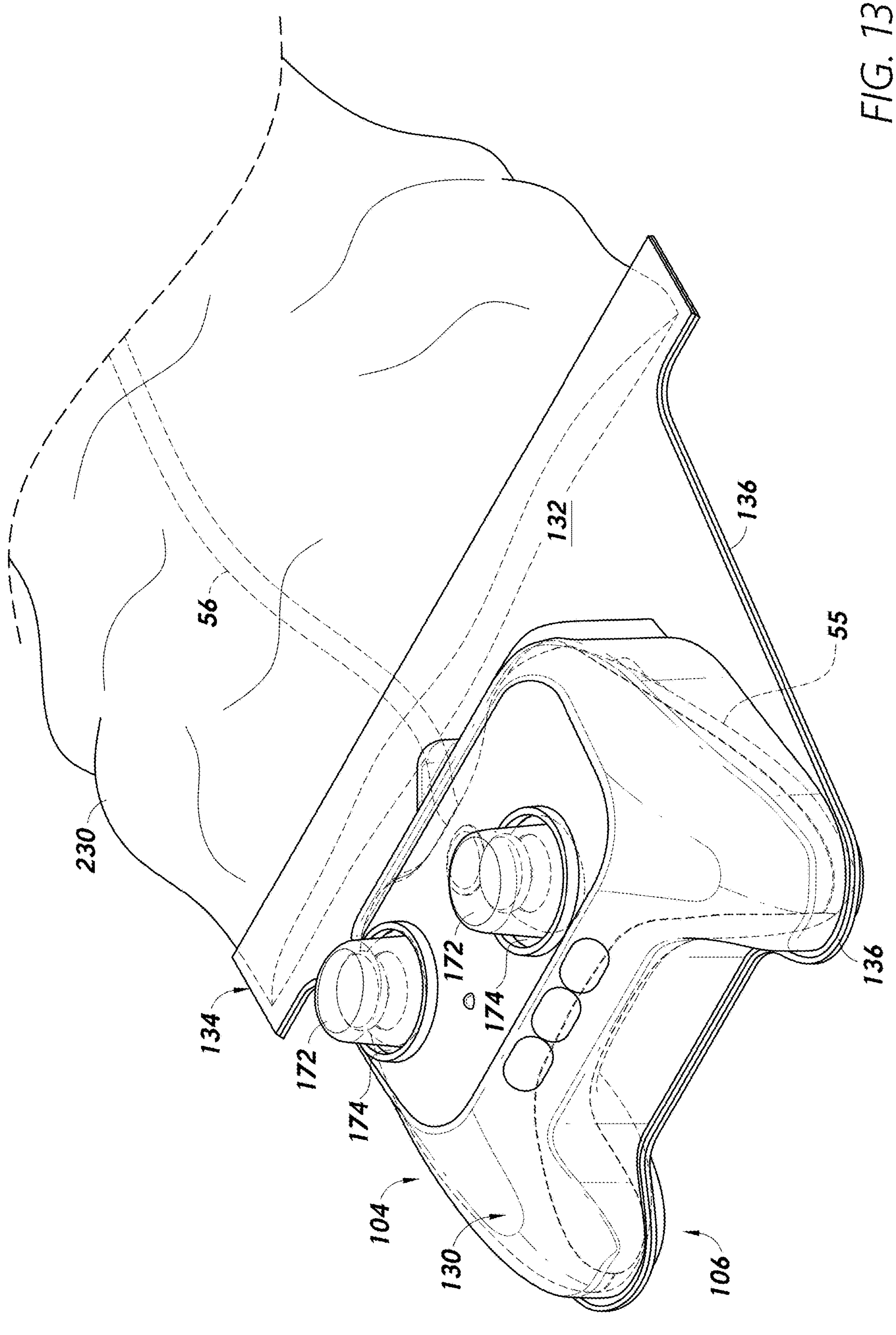
FIG. 13 illustrates a view of an example controller wrapped in an embodiment of a sterile drape, with the sterile drape being interfaced with another sterile barrier within the sterile field.

Referring to FIG. 13, in some cases, the drape 102 can be coupled to another sterile barrier within the sterile surgical field. The apron 132 of the drape 102 includes an interface 134 comprising an area at the distal portion of the second part 110 of the first sheet 104 and the second part 120 of the second sheet 106 (e.g., the planar envelope or apron 132), at the opening 138 of the drape 102. In various examples, the interface 134 comprises between 1 to 5 inches (e.g., 3 to 4 inches) of the apron 132, at the distal edge of the apron 132. The interface 134 can be coupled to another sterile barrier such as another wrap, drape, sheet, etc. to continuously extend the protection of the drape 102 to the other sterile barrier. For instance, the opening 138 at the interface 134 can be aligned to a similar opening at the adjacent sterile barrier, and the corresponding materials of the drape 102 and the other sterile barrier can be overlapped and sealed. The interface 134 can be coupled to the other sterile barrier using a heated sealing device, a laser-based device, an ultrasound sealing device, or like device, that melts (or welds, etc.) the material of the first sheet 104 and the second sheet 106 to the material of the other sterile drape. Alternately or additionally, adhesives or other substances that form a similar bond can be used to couple the drape 102 to the other sterile barrier.

In various implementations, an example sterile drape 102 can have three or more side edges plus the opening 138. In the examples shown in the figures (see FIGS. 7-10 for example), the sterile drape 102 has generally four side edges, including the opening 138. For instance, the sterile drape 102 is illustrated as having a generally trapezoidal shape (in a plan view). In other examples, a sterile drape 102 may have more than four side edges. In some examples, the sterile drape 102 may have at least one set of opposing side edges. In other examples, the sterile drape 102 may not have any opposing side edges. In alternate implementations, depending on the implement to be wrapped, an example sterile drape 102 can have a generally elliptical shape (in a plan view), polygonal shape, or other shape, including irregular shapes.

The sterile drape 102 comprises at least two thermoformed (or the like) sheets of a thermoplastic polymer, such as thermoplastic polyurethane (TPU) for one example. Another example can include polyethylene terephthalate glycol (PETG). Polystyrene or other polymers may also be used for at least one of the sheets (104 and 106), as well as various other composites or other materials. TPU can be used advantageously due to its chemical resistance, durability, formability, impact and temperature resistance, and other properties. TPU can be made transparent for ease of visibility through the drape 102. The material(s) used for the drape 102 promote a thin and robust barrier that is strong and flexible, giving the drape 102 a tactile feel and making it easier to grip the implement. For example, adding the drape 102 can improve the grip and handling of the implement for the user. The material(s) used for the drape 102 also provide for haptic feedback through the drape 102 to the user. Further, the material(s) used for the drape 102 are sterile or are capable of being sterilized, and are configured to maintain sterility during and after stress. At least the first sheet 104 can comprise TPU film. In some cases, the first sheet 104 and the second sheet 106 comprise TPU film. In other cases, the second sheet 106 is formed from a different material than the first sheet 104. For instance, the second sheet 106 may be formed from a material such as a polymer or composite that enhances the grip of the implement.

The sterile drape 102 can be thermoformed in two processes (one for the first sheet 104 and one for the second sheet 106). For example, the sterile drape 102 may be vacuum and pressure formed with a pair of dies (or molded using a pair of molds with vacuum holes) to produce the first sheet 104 and the second sheet 106. This results in few thermoforming tools, for reduced development and manufacturing processes and a greater cost savings. The contours (112 and 122) and features 170 can be formed as part of the process of forming the first sheet 104 and the second sheet 106. In an example, the hollow protrusion 172 and the trough 174 can be formed together, via the die or mold, by deforming the sheet(s) of polymer at the various locations. This results in each trough 174 being collinear with a hollow protrusion 172 for consistent performance.

3. Implementing Systems and Terminology

Implementations disclosed herein provide systems, methods and apparatus for image-based localization and navigation for robotically-controlled or user-controlled medical instruments. Various implementations described herein provide for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A sterile drape for a medical implement, comprising:

a first sheet, including:

- a first part of the first sheet having first contours configured to conform to a first surface of the medical implement, and
- a second part of the first sheet comprising a planar extension of the first part of the first sheet;

a second sheet, including:

- a first part of the second sheet having second contours configured to conform to a second surface of the medical implement, and a second part of the second sheet comprising a planar extension of the first part of the second sheet;

a seal extending along a first portion of a perimeter of the first sheet and along a corresponding first portion of a perimeter of the second sheet, sealing the second sheet to the first sheet along the seal and thereby forming a cavity between the first part of the first sheet and the first part of the second sheet;

an opening extending along a second portion of the perimeter of the first sheet and along a corresponding second portion of the perimeter of the second sheet, the opening comprising an access to the cavity, via the second part of the first sheet and the second part of the second sheet; and an interface for coupling the sterile drape to a sterile barrier, the interface disposed at a distal portion of the second part of the first sheet and the second part of the second sheet, at the opening.

2. The sterile drape for a medical implement of claim 1, further comprising a hollow protrusion at the first part of the first sheet, configured to receive and to conform to an input device of the medical implement.

3. The sterile drape for a medical implement of claim 2, further comprising a trough at a base of the hollow protrusion and around a perimeter of the hollow protrusion, wherein the trough comprises slack material concentrated at the base of the hollow protrusion and around the perimeter of the hollow protrusion.

4. The sterile drape for a medical implement of claim 1, further comprising an apron comprised of the second part of the first sheet and the second part of the second sheet, the apron configured to cover an associated component of the medical implement.

5. The sterile drape for a medical implement of claim 1, further comprising a protruding cord notch disposed at the first part of the first sheet and extending partly into the second part of the first sheet.

6. The sterile drape for a medical implement of claim 1, wherein at least the first part of the first sheet is transparent to visible light.

7. The sterile drape for a medical implement of claim 1, wherein the perimeter of the second sheet is aligned to the perimeter of the first sheet, and wherein the first sheet is sealed to the second sheet along a front edge of the cavity, without sealing side edges or a back edge of the cavity.

8. A system, comprising:

a controller for a mechanically-enabled apparatus; and a sterile drape encasing the controller, comprising:

a first sheet, including:

a first part of the first sheet having first contours configured to conform to a first surface of the controller, and a second part of the first sheet comprising a planar extension of the first part of the first sheet;

a second sheet, including:

a first part of the second sheet having second contours configured to conform to a second surface of the controller, and a second part of the second sheet comprising a planar extension of the first part of the second sheet;

a seal extending along a first portion of a perimeter of the first sheet and along a corresponding first portion of a perimeter of the second sheet, sealing the second sheet to the first sheet along the seal and thereby forming a cavity for the controller between the first part of the first sheet and the first part of the second sheet; and an opening extending along a second portion of the perimeter of the first sheet and along a corresponding second portion of the perimeter of the second sheet, the opening comprising an access to the cavity, via the second part of the first sheet and the second part of the second sheet.

9. The system of claim 8, further comprising an interface for coupling the sterile drape to a sterile barrier, the interface disposed at a distal portion of the second part of the first sheet and the second part of the second sheet, at the opening.

10. The system of claim 8, further comprising a hollow protrusion at the first part of the first sheet, configured to encase and to conform to a joystick of the controller, and a trough at a base of the hollow protrusion and around a perimeter of the hollow protrusion, the trough comprising slack material concentrated at the base of the hollow protrusion and around the perimeter of the hollow protrusion as a relief.

11. The system of claim 10, wherein the slack material is configured to become less slack in a first direction when the joystick is moved in an opposite direction, allowing the joystick to be moved in the first direction without putting tension on a remainder of the first part of the first sheet.

12. The system of claim 8, further comprising one or more raised features on the first part of the first sheet, configured to conform to corresponding control or indication components of the controller.

13. The system of claim 8, further comprising one or more tactile areas on the first part of the first sheet, configured to allow user-operation of touch-sensitive controls on the controller.

14. The system of claim 8, wherein at least a portion of the first part of the first sheet is transparent to visible light.

15. A sterile drape for a medical implement, comprising:

a cavity configured to conform to an outer surface of the medical implement and to encase the medical implement;

a planar envelope extending laterally from the cavity, with access to the cavity; and an opening at a distal portion of the planar envelope and configured to provide access to the cavity via the planar envelope.

16. The sterile drape for a medical implement of claim 15, further comprising an interface for coupling the sterile drape to a sterile barrier, the interface extending along a distal edge of the planar envelope, at the opening.

17. The sterile drape for a medical implement of claim 15, further comprising a hollow protrusion from a first surface of the cavity, the hollow protrusion configured to receive and to conform to an input device of the medical implement.

18. The sterile drape for a medical implement of claim 17, further comprising a trough at a base of the hollow protrusion and around a perimeter of the hollow protrusion, the trough comprising slack material concentrated at the base of the hollow protrusion and around the perimeter of the hollow protrusion.

19. The sterile drape for a medical implement of claim 15, further comprising a first sheet of a first material, at least a portion of the first sheet being transparent to visible light, and a second sheet of a second material, and wherein the first sheet and the second sheet are stacked and sealed to form the cavity and the planar envelope.

20. The sterile drape for a medical implement of claim 19, wherein the first material and the second material are sterile or are capable of being sterilized, and wherein the first material and the second material are configured to maintain sterility during and after stress.

* * * * *